United States Patent [19]

Gunderson

[11] 4,446,743
[45] May 8, 1984

[54] METHOD AND APPARATUS FOR EDGEWISE COMPRESSION TESTING OF FLAT SHEETS

[75] Inventor: Dennis E. Gunderson, Madison, Wis.

[73] Assignee: The United States of America as represented by the Secretary of Agriculture, Washington, D.C.

[21] Appl. No.: 366,754

[22] Filed: Apr. 8, 1982

Related U.S. Application Data

[63] Continuation-in-part of Ser. No. 152,874, May 23, 1980, Pat. No. 4,343,189.

[51] Int. Cl.³ ............................................. G01N 11/00
[52] U.S. Cl. ........................................ 73/822; 73/856
[58] Field of Search ................. 73/822, 818, 856, 826, 73/831

[56] References Cited

U.S. PATENT DOCUMENTS 2,350,060  5/1944  Montgomery ...................... 73/818
2,368,400  2/1945  Templin ............................. 73/818
3,316,757  5/1967  Fletcher et al. .................... 73/826

OTHER PUBLICATIONS

Stockmann, V. *Measurement of Intrinsic Compressive Strength of Paper,* In Tappi, 59(7): p. 93, 1976.
Fellers, C., and P. Jonsson, *Compression Strength of Liner-board and Corrugated Medium—An Analysis of Testing Methods* (Swedish), In Svensk Papperstidning, 78(5): p. 172, 1975.
Seth, R. S., and R. M. Soszynski, *The Intrinsic Edgewise Compressive Strength of Paper: An Evaluation of Methods,* In Tappi, 61(10): p. 125, 1979.
Ramberg, W., and J. A. Miller, *Determination of Presentation of Compressive Stress–Strain Data for Thin Sheet Material,* In Journal of Aeronautical Sciences, 13(11): p. 569, 1946.

Primary Examiner—Anthony V. Ciarlante
Attorney, Agent, or Firm—M. Howard Silverstein; David G. McConnell

[57] ABSTRACT

A compressive creep test fixture of box-like structure having a rectangular opening for testing a specimen and a pair of ports for applying a vacuum is provided. Rigid or semi-rigid elements, spaced from each other in a uniform manner, support the specimen at the rectangular opening during testing. The vacuum in the fixture holds the tested specimen in place on the support elements, and together the vacuum and support elements prevent buckling of very thin sheet materials under conditions of edgewise compressive loading.

A method for using a compressive creep test fixture to determine mechanical properties of sheet materials.

4 Claims, 7 Drawing Figures

METHOD AND APPARATUS FOR EDGEWISE COMPRESSION TESTING OF FLAT SHEETS

BACKGROUND OF THE INVENTION

This application is a continuation-in-part of application Ser. No. 152,874, filed May 23, 1980. U.S. Pat. No. 4,343,189.

(1) Field of the Invention

The invention deals with an apparatus for and a method of determining the mechanical properties of sheet materials under conditions of edgewise compressive loading.

(2) Description of the Prior Art

Thin sheets of materials such as paper or cardboard are frequently used in packaging or other applications where their mechanical properties—such as modulus of elasticity, ultimate strength, strain to failure, creep rate and dimensional stability—are important. In attempting to test a thin sheet specimen in edgewise compression, unless adequate lateral restraint is provided, the sheet shifts out of plane or "buckles" at such a light load that is impossible to determine the engineering properties of the material. The testing and buckling of such sheets can be understood simply by grasping an ordinary sheet of paper, placing one hand on one width of the paper and the other hand on the other width. Moving one's hands towards each other is analogous to applying an edgewise compressive loading to this sheet, and the results are the same in each case. The sheet will shift laterally, or buckle out of plane.

In order that measurements of such sheet materials' properties can be made, various methods are currently used. One alternative is to roll the sheets into tubes or cylinders and provide them with internal support. Secondly, the span or length of the specimen is shortened to the point where buckling does not occur. Thirdly, the sheet is restrained between two flat plates. Finally, the sheet is restrained between an array of fingers on each side of the specimen sheet. These fingers deflect with the sample as it undergoes strain in the direction of loading, but provide restraint against lateral motion. These methods, however, have several significant shortcomings.

When a sheet must be rolled to form a cylinder before testing, undesirable transverse stresses occur. When a specimen is unduly short, measurement of its properties cannot be made on its body but must instead be made on the clamps holding the specimen in place.

Errors in measurement are then possible due to clamping effects on the paper, restraint of deformation in the transverse direction, and slipping of the specimen in the clamps. When a specimen is tested between two flat plates, frictional forces must occur but cannot be accurately measured. Finally, measurement of the properties of a specimen held on both sides by fingers can also not be made on the specimen body, resulting in errors of the same kind as those occuring in measurement of a very short specimen's properties.

SUMMARY OF THE INVENTION

The invention is a method and apparatus for edgewise compression testing of a flat sheet, in which the sheet is prevented from buckling in the lateral direction by a sheet-supporting surface, flexible in the directions of test loading, on the first side of the sheet; and by air pressure on the other side of the sheet in excess of the air pressure on the first side of the sheet. The sheet is maintained in place on the testing apparatus by holding means. The apparatus further includes means for placing a load on the sheet in a desired direction.

The method and apparatus are particularly useful in measuring physical properties, such as modulus of elasticity, ultimate strength, strain to failure, creep rate, and dimensional stability, of thin sheets. When measurements for such properties are attempted on thin sheets with conventional apparatus, there is a tendency for the sheets to "buckle" or shift out of plane laterally, making measurement of such properties impossible.

Accordingly, an object of this invention is an apparatus and method for providing the lateral support necessary to prevent the sheet from shifting out of plane when loaded in an edgewise compressive manner, in order that the engineering properties of the sheet material may be determined. A further object of the invention is a sheet testing method which leaves the full face of the sheet exposed and flat. This sheet configuration allows strain measurement directly on the specimen by a variety of means; and exposes the full sheet uniformly to changes in ambient humidity, which is a significant advantage in cyclic creep testing.

A still further object of this invention is a method of providing a lateral support force which is uniform over the complete test specimen regardless of variations or changes in specimen thickness. A final object of the invention is a method of testing whose restraint system is entirely independent of the loading mechanism and the strain measuring technique, so that the method will be equally applicable to biaxial as well as uniaxial loading.

DESCRIPTION OF THE PREFERRED EMBODIMENTS

The testing of thin sheet materials for some mechanical properties has heretofore been difficult because of the sheets' tendencies to buckle during testing. The apparatus and testing method described herein remove these difficulties.

Figures 1, 2, 3:
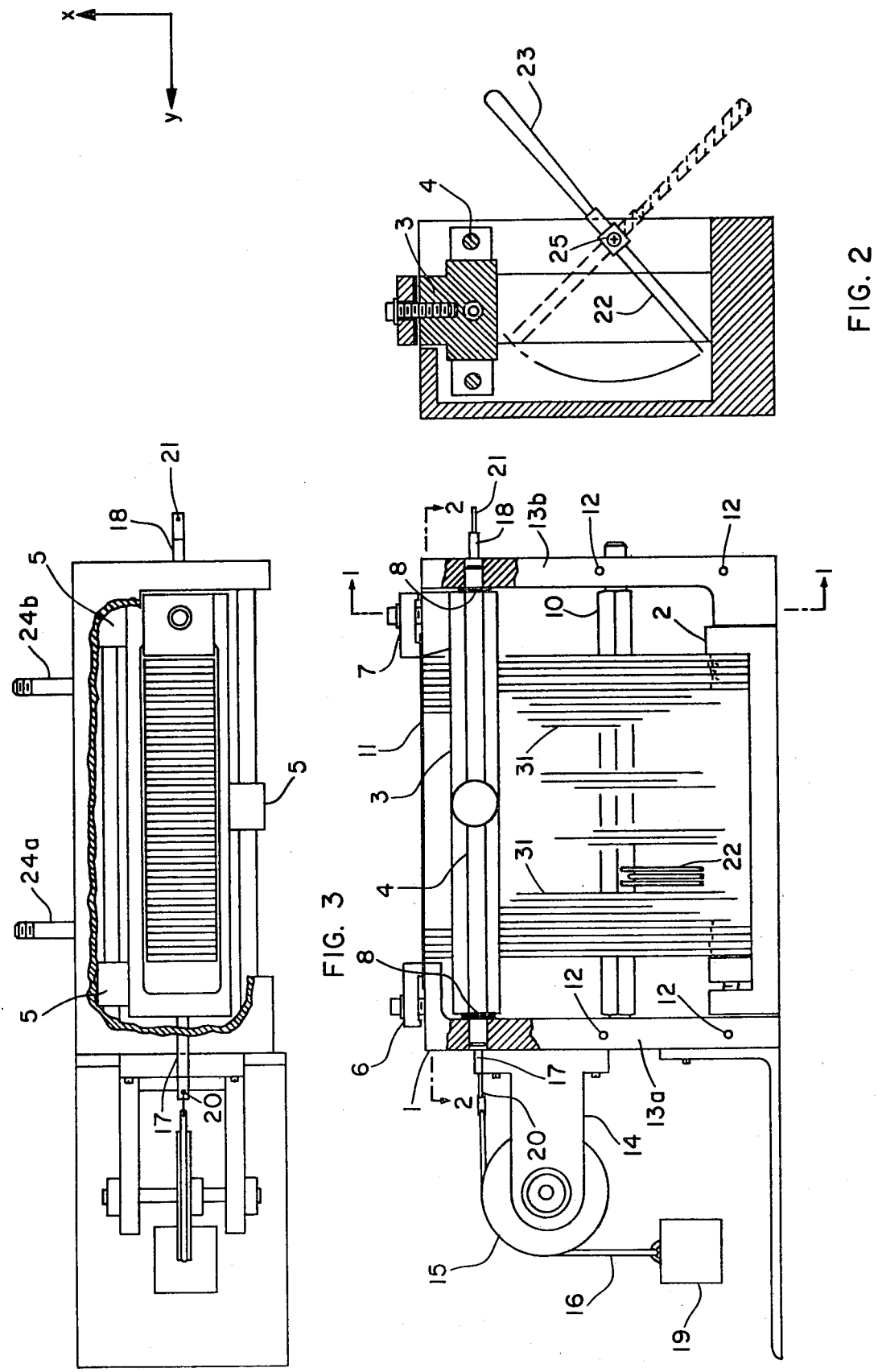
FIG. 1 is a front sectional view of the apparatus constructed to embody the preferred teaching of the present invention.
FIG. 2 is a side sectional view of the apparatus of FIG. 1, along a line corresponding to line 1—1 of FIG. 1.
FIG. 3 is a top sectional view of the apparatus of FIG. 1, along a line corresponding to line 2—2 of FIG. 1.

The apparatus, called a compressive creep test fixture, that comprises the preferred embodiment of this invention is enclosed in a box-like structure. Referring now to FIGS. 1 and 2, housing 1 and cover (not shown) would be seen to form a completely closed box except for a rectangular opening at the top of the apparatus.

The cover would be located in FIG. 1, and would remove from view the interior of the apparatus now visible because of its absence. It would be secured in place with screws or other fastening means and attached to housing 1 at the four threaded holes 12. Two of these threaded holes 12 are located in each of the two housing side walls 13a and 13b.

A support assembly 2 is comprised of a plurality of steel leaves 31 separated by spacers at their base, where they are clamped together and supported. For the linerboard materials tested with the apparatus, the steel leaves used are 4.5 inches in length, 1.0 inch wide, and 0.010 inch thick, and are separated by the spacers at a distance of 0.047 inch center to center.

The leaves are meant to support the specimen 11 during testing in the lateral direction, but should flex in the direction of testing with very little resistance. This ease of flex in the test direction minimizes the effects of the leaves on values obtained during testing for physical properties. The length, width, thickness, material, and spacing of the leaves are all variable to achieve adequate strength to provide the required lateral support and to minimize the contribution to edgewise loading due to forces required to flex the leaves.

The rectangular opening at the top of the apparatus, as seen in FIG. 3, reveals the tops of the leaves. The specimen 11 to be tested is placed on the leaves at the rectangular opening. The specimen 11 substantially covers the rectangular opening, obscuring the leaves from view and creating a closed box. The specimen 11 in place on the rectangular opening, by substantially closing the apparatus, permits a pressure differential to be created between the inside and outside of the apparatus.

A fixed-end clamp 6 and a movable clamp 7, as shown in FIG. 1, prevent the movement of the specimen 11 in the test directions. The movable clamp 7 is affixed to the carriage 3. The carriage 3 when viewed from the top is a rectangular piece with a section in the middle cut out to reveal the tops of the leaves. The carriage 3 is slightly shorter than the inside length of the test fixture to allow the carriage 3 to move within the test fixture. Adjacent to the carriage 3, in the two spaces between the carriage 3 and the two lengthwise walls of the fixture, and parallel to the length of the test fixture, are two cylindrical guide rods 4. Each guide rod 4 is anchored in the housing 1 at a point in each of the two housing side walls 13a and 13b. The guide rods 4 are prevented from moving in place by snap rings 8. A snap ring 8 is placed at the inside wall at each point where a guide rod 4 enters a housing side wall 13.

Along either side of the length of the carriage 3, a plurality of adjustable slides 5 are attached to the carriage 3. In the preferred embodiment, one slide 5 is shown on one side of the carriage 3 and two slides 5 are shown on the other side. The adjustable slides 5 each contain an opening large enough to accommodate the diameter of the guide rod 4. The guide rod 4 passes through the opening of the adjustable slide 5. In this manner, the carriage 3, to which the adjustable slides 5 are attached, can move on the guide rods 4 to the limit of the carriage's 3 travel. The carriage 3 is constructed of a length such that it can move about 0.100 inch within the interior of the test fixture and along the guide rods 4. Thus, while the carriage 3 is in the position depicted by FIG. 1, with approximately equal distances between the ends of the carriage 3 and the two housing side walls 13a and 13b, the carriage 3 can move 0.050 inch along the guide rods 4 in either direction before being stopped by a housing side wall 13. As the movable clamp 7 is directly attached to the carriage 3, it also moves these distances. During a compression test of a specimen 11 held between the two clamps, the movable clamp 7 will move slightly towards the fixed-end clamp 6, and the carriage 3 as shown in FIG. 1 will move to the left of the guide rods 4. During a tension test, the movable clamp 7 will move slightly away from the fixed-end clamp 6, and the carriage 2 as shown in FIG. 1 will move to the right on the guide rods 4.

Tension or compression of a given magnitude may be put on a specimen 11 in many ways. One way is with a simple weight 19 and pulley 15 mechanism. The weight 19 and pulley 15 shown in FIG. 1 are positioned to place a compression load on the specimen 11. The pulley 15 is supported by a bracket 14, and the bracket 14 is attached to the housing side wall 13a by a plurality of bolts, screws or other attaching means. A compression lead 17 passes through a cavity in the housing side wall 13 nearest the bracket in the position as shown in FIG. 1. The compression lead 17 is a rectangular or cylindrical piece with a hole 20 at one end and threads at the other, the threaded end being attached to carriage 3. The hole 20 is used to tie a string 16 to the compression lead 17. The string 16 passes over the pulley 15, and the end of the string 16 not attached to the compression lead 17 is attached to the weight 19 of a size necessary to put the desired compression on the specimen 11. The weight 19 places a compression load on the specimen 11 by pulling on the compression lead 17, which shifts the carriage 3 as shown in FIG. 1 to the left, which in turn moves the movable clamp 7 to the left. The compression strain of the specimen may be measured by an extensometer placed directly on the specimen 11, in a manner well known to those skilled in the art.

Tension may be placed on the specimen 11 in a similar manner. The attaching means holding the bracket 14, as shown in FIG. 1, are removed and the bracket 14 is moved to the opposite housing side wall 13b. This housing side wall 13b is similar to housing wall 13a in that it is also provided with threaded holes such that bolts, screws, or other attaching means may be used to attach bracket 14 to housing side wall 13b. A tension lead 18 is identical to compression lead 17 in construction, as described hereinabove. The threaded end of the tension lead 18 is attached to the carriage 3 along the carriage's 3 width at a point near the housing side wall 13b. The tension lead 18 passes through a cavity in housing side wall 13b. The hole 21 of the tension lead 18 thus is visible outside of the test fixture and available for use in attaching the weight 19 with the string 16.

It is important that the leaves that are part of the support assembly 2 and which support the specimens 11 are spaced equidistantly. This is important because the equidistantly-spaced leaves provide enough support so that a thin specimen 11 will not collapse in the spaces between the leaves. Spacing the leaves unevenly, of course, results in some spaces between leaves being larger than anticipated by the design of the test fixture. These large spaces are where the specimen 11 is likely to collapse upon application of a compressive load, and such collapse would render the test meaningless. The leaves, being able to flex in the direction of testing, have a tendency to become irregularly spaced at their highest points, that is, where the leaves contact the specimen 11. In order that the leaves may become realigned and to ensure their uniform spacing during testing, the test fixture is provided with an alignment comb 10.

The alignment comb 10 is a toothed, pivotable shaft able to be actuated from the outside of the test fixture with the alignment comb actuator 23. A plurality of teeth 22 equal to the number of leaves 31 are attached to the shaft of the alignment comb 10 at regular intervals. The space between each of the teeth 22 is approximately equal to the thickness of the leaves. Referring now to FIG. 2, the alignment comb actuator 23 is seen in its normal position. The shaft of the alignment comb 10 is perpendicular to the head of the phillips-head screw 25 seen at the right-hand side of the figure. With the actuator 23 in this normal position, the teeth 22 of the alignment comb 10 are in contact with the leaves only at their very bottom. When the actuator 23 is grasped and rotated clockwise, the teeth 22 further engage the leaves. With each tooth 22 being approximately the same diameter as the space between the leaves, and the space between the teeth 22 being approximately the same as the thickness of the leaves, the comb 10 while being rotated clockwise creates uniform spacing between the leaves. Because of the tightness of the fit when the teeth 22 engages the leaves with the actuator 23 turned clockwise, the actuator 23 may be released and the comb 10 will still engage the leaves. It is advisable that the comb 10 engage the leaves until after a vacuum has been placed on the test fixture.

A vacuum is placed on the test fixture through vacuum fittings 24a and 24b. The vacuum suitable for the linerboard materials that were tested with the apparatus was 5 in. Hg. This vacuum can be measured by a gauge placed on the body of the apparatus, which could be attached to the test fixture through a fitting similar to the vacuum fittings 24. It is necessary to place a vacuum on the test fixture because the resulting difference in pressure on the two sides of the specimen 11 prevents that specimen's 11 collapse upon application of a test load. It is also necessary that the teeth 22 of the alignment comb 10 engage the sleeve until the application of the vacuum. If there was no aligning force on the leaves such as the alignment comb 10 provides, the specimen 11 in place at the top of the leaves while being "pulled into" the test fixture by the vacuum could shift the leaves somewhat, creating unequal spacing between the leaves that is undesirable for the reasons cited hereinabove.

Thus, the testing method is as follows. First, the specimen 11 is placed at the top of the leaves and fixed in place with the movable 7 and fixed-end 6 clamps. This substantially closes the test fixture in that the specimen 11 covers its only opening. Second, the alignment comb 10 is made to engage the leaves by rotating the alignment comb actuator 23 clockwise. Third, the appropriate vacuum is applied to the test fixture. Fourth, the alignment comb 10 is swung back to its normal, non-engaged position. The alignment comb 10 must be returned to its normal position, because while it is engaged it would prevent the leaves from flexing in the direction of applied load. This lack of leaf flexibility would adversely affect the test results. The alignment comb 10 may safely be returned to its normal position after the vacuum has been applied, as leaf spacing will not shift once the specimen 11 is in place on the leaves in the evacuated test fixture. Fifth, an extensometer is placed on a specimen to measure its deformation. Finally, the test is conducted on the specimen 11 using the weight 19 and pulley 15 of the embodiment, or some other load-applying means.

Figure 5:
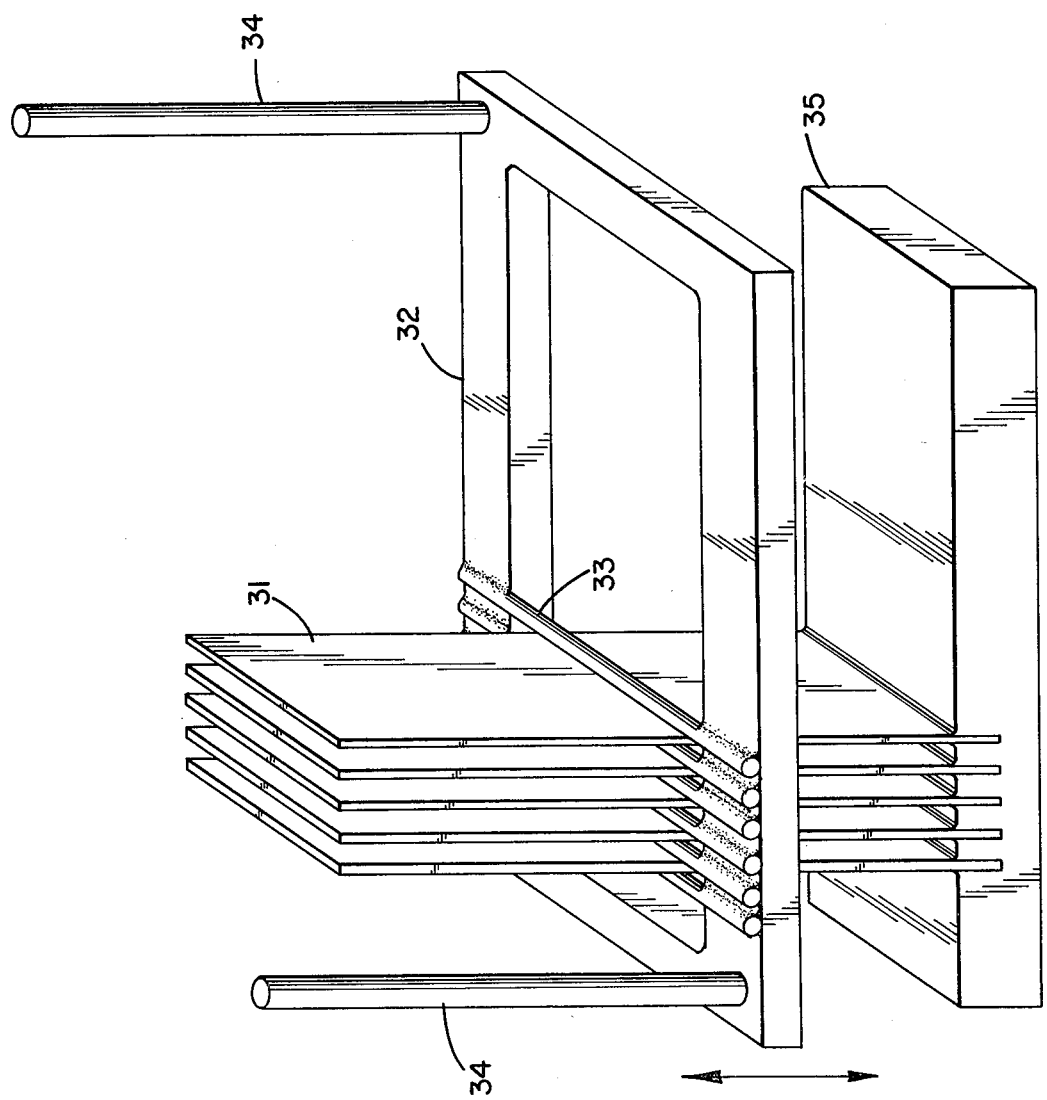
FIG. 5 shows an alternate means to align the apparatus shown in FIGS. 1, 2 and 3.

Referring now to FIG. 5, another means to space the leaves 31 equidistantly comprises an alignment frame 32 surrounding the leaves 31 and located within housing 1, not shown. A plurality of wires 33 are attached at either end to opposite sides of alignment frame 32. The wires 33 are spaced at regular intervals with each wire 33 located between two of the leaves 31. Arms 34 are provided to raise and lower alignment frame 32 relative to the leaves 31. When the alignment frame 32 is in the raised position close to the highest point of the leaves 31 the wires 33 restrain the leaves 31 from flexing and align the leaves 31 so as to provide an equal support spacing while the specimen is placed in position.

Once the specimen is in position the test fixture is substantially closed. Next a vacuum is drawn on the test fixture as described previously. The alignment frame 32 is then lowered by means of the arm 34 which extend through clearance holes in the housing 1, not shown. When the alignment frame 32 is lowered toward the base 35 wherein the leaves 31 are clamped the leaves 31 are free to flex in the direction of the applied load.

The apparatus of FIGS. 1-3 contains leaves capable of flexing solely in the y-direction, as that direction is defined in the vectors to the right of FIG. 3. If testing is desired in the x-direction as well, such an apparatus would be unsuitable because the leaves shown would not flex in the x-direction and this inability to flex would adversely affect the x-direction test results.

Figure 4:
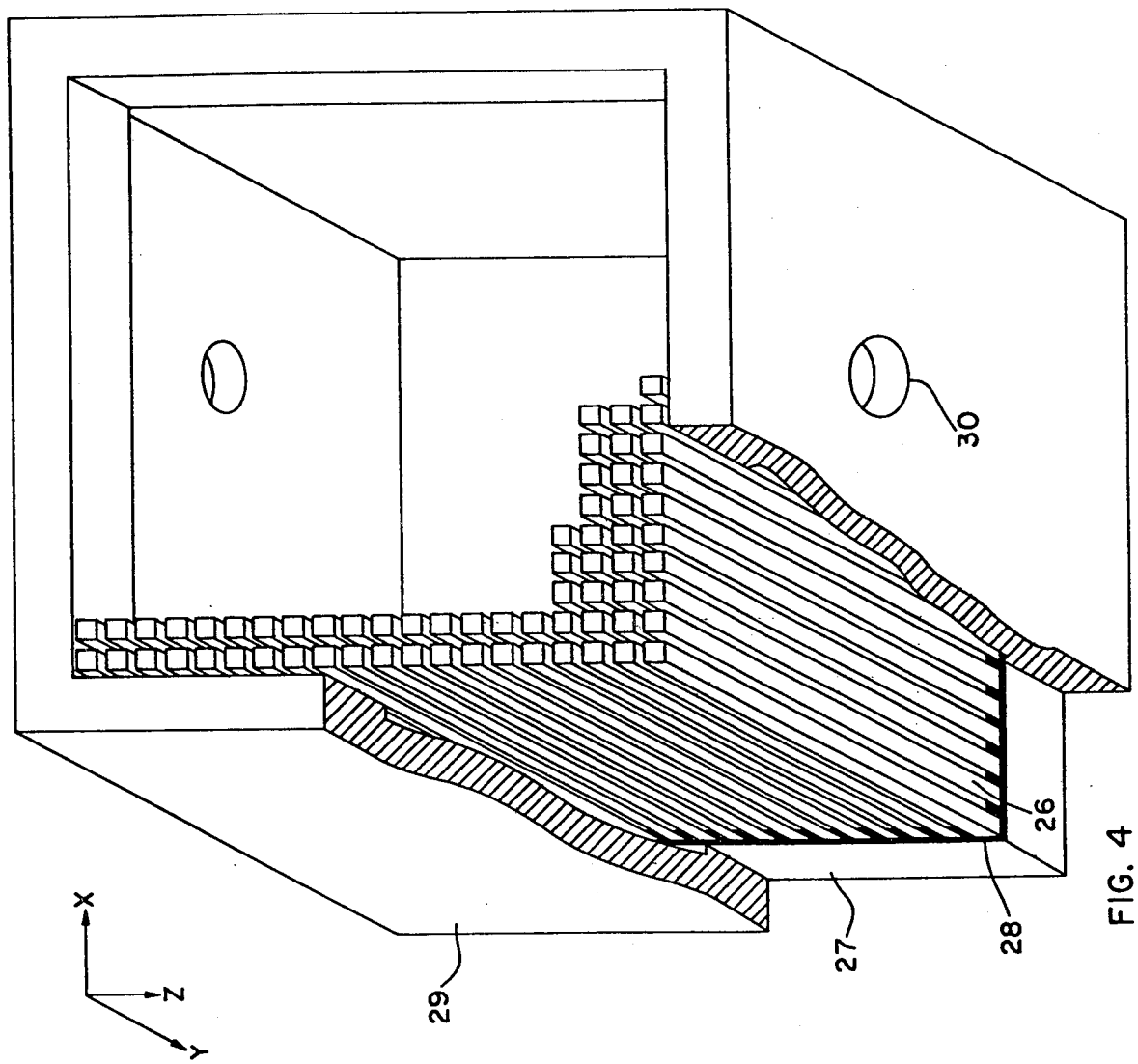
FIG. 4 is a perspective sectional view of an alternate embodiment of the present invention.
Figure 4:
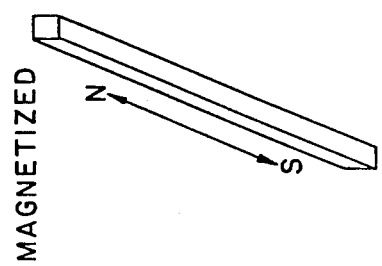

Freedom in both the x- and y-direction is provided by the alternate embodiment of FIG. 4, which may be referred to as the planar restraint table. In this design, each leaf is replaced by a plurality of rigid columns 26, each of which is free to pivot in all directions at this base. In this alternate embodiment, pivot flexibility is provided by bonding the columns 26 to the base 27 with a flexible elastomer 28. Alignment of the rigid columns 26 is achieved by magnetizing each column 26 as shown. The repulsion of like poles causes the columns 26 to space themselves evenly across the field. The array of columns 26 is contained by the housing 29. These elements comprise a closed box similar to the compressive creep test fixture. A simple, similar to the preferred embodiment's specimen 11, is placed across the flat tops of the columns 26. A vacuum is drawn at the ports 30 and the resulting pressure differential across the sample holds it in place across the tops of the columns 26. Any of several techniques well-known in the art may be used to apply edgewise loads to the specimen.

Another embodiment of the planar restraint table of FIG. 4 would comprise electromagnetizing each column 26 by means of a direct current excited core wound around each column rather than be permanently magnetizing each element. The advantage of this alternative design is that once alignment was achieved and the differential pressure applied, the magnetizing current could be removed. With removal of the magnetic forces between the columns 26, the sheet would be free to move in the x- and y-directions substantially free of restraint from the support mechanism.

Figure 7:
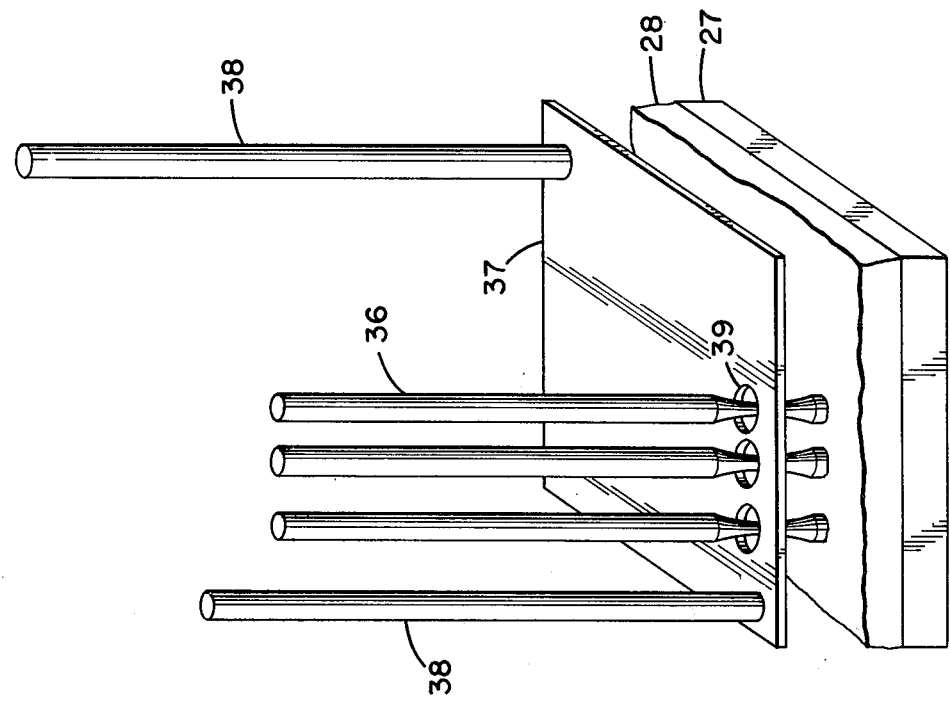
FIG. 7 shows the lowered position of an alternate means to align the apparatus of the alternate embodiment shown in FIG. 4.
Figure 6:
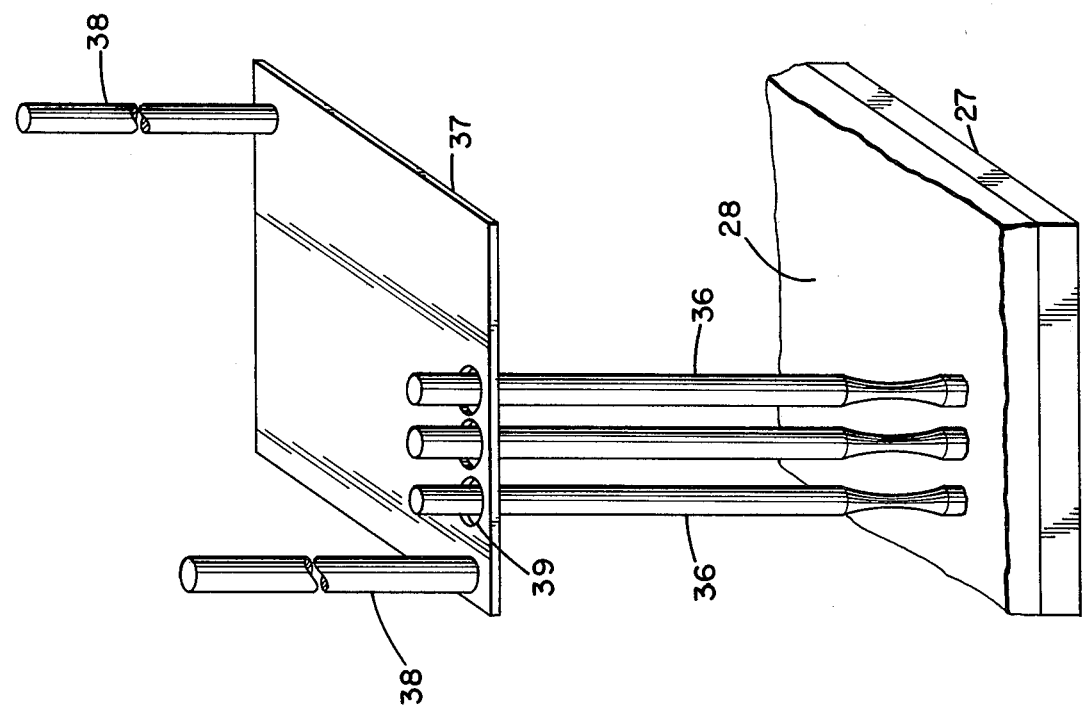
FIG. 6 shows the raised position of an alternate means to align the apparatus of the alternate embodiment shown in FIG. 4.

An alternative to aligning the columns by means of magnetization is illustrated in FIGS. 5, 6 and 7. In these embodiments the diameter of the column 36 at its free end is greater than the diameter of the column 36 at the end placed in the elastomer 28. An alignment plate 37 is provided, located within housing 29, not shown. Levers 38 are provided to raise and lower alignment plate 37 relative to the columns 36. The alignment plate 37 has on its surface a plurality of apertures 39 spaced equidistantly. Each aperture 39 is of a diameter such that the free end of one of the columns 36 can fit snugly therein. When the alignment plate 37 is placed within the housing 29 in the raised position close to the free end of the columns 36 each column 36 fits into one of the equidistant apertures 39 thereby aligning all the columns 26 equidistantly so that a sample to be tested can be placed across the flat tops of the columns 36.

Once the specimen is positioned a vacuum is drawn on the test fixture as described previously. The alignment plate 37 is then lowered toward the base 27 by means of levers 39 which extend through clearance holes in the housing 29, not shown. When the alignment plate 37 reaches the level corresponding to the decreased diameter portions of the columns 36 the apertures 39 will be of greater diameter than the columns 36 and the columns 36 in the flexible elastomer 28 will be free to flex in the x- and y-directions within each aperture 39.

Another alternative embodiment of the planar restraint table of FIG. 4 comprises replacing the rigid columns 26 with a larger number of flexible wires or fibers, which would simply bend as the sample moved in the x-y plane.

I claim:

1. An apparatus for edgewise compression testing of a flat sheet, comprising:
    (a) means for restraining said sheet from buckling in the lateral direction, comprising:
        (1) a sheet-supporting surface, flexible in the directions of test loading, on one side of said sheet, comprising:
            (a) a plurality of lateral support leaves capable of being easily flexed in one test direction;
            (b) spacing means at the base of said leaves whereby said leaves are clamped together and supported;
            (c) enclosure means substantially surrounding said leaves such that a specimen in a position to be tested on said leaves comprises a boundary between said enclosure means at a lower air pressure and the ambient at a higher air pressure, and to which enclosure means said spacing means are attached; and
            (d) aligning means for providing a fixed spacing between said leaves, comprising:
                (1) an alignment frame located inside said enclosure means and surrounding said leaves;
                (2) a plurality of wires stretched across said alignment frame equidistantly, each wire having one end attached to one side of aid alignment frame and the other end attached to the opposite end of said alignment frame, with each wire located between two of said leaves; and
                (3) means for raising and lowering said alignment frame;
        (2) air pressure on the unsupported side of said sheet exceeding that on the support side of said sheet;
    (b) means for holding said sheet adjacent to said restraining means during testing; and
    (c) means for placing a load on said sheet in a desired direction.

2. An apparatus for edgewise compression testing of a flat sheet, comprising:
    (a) means for restraining said sheet from buckling in the lateral direction, comprising:
        (1) a sheet-supporting surface, flexible in the directions of test loading, on one side of said sheet, comprising:
            (a) a plurality of semi-rigid columns, free at one end, capable of being easily flexed at their bases in all directions and with the free end of each column having a greater diameter than the other end of each column;
            (b) attaching means for fixing the non-free end of said rigid columns;
            (c) enclosure means substantially surrounding said columns such that a specimen in a position to be tested on said columns comprises a boundary between said enclosure means at a lower air pressure and the ambient at a higher air pressure; and
            (d) spacing means for ensuring that said columns be spaced evenly across the field of columns; comprising:
                (1) an alignment plate located inside said enclosure means, said alignment plate having a plurality of apertures spaced equidistantly thereon, each aperture being of a diameter such that the free end of one of said columns can fit snugly therein; and
                (2) means for raising and lowering said alignment plate;
        (2) air pressure on the unsupported side of said sheet exceeding that on the supported side of said sheet;
    (b) means for holding said sheet adjacent to said restraining means during testing; and
    (c) means for placing a load on said sheet in a desired direction.

3. A method for edgewise compression testing of a flat sheet, comprising:
    (a) restraining said sheet from buckling in the lateral direction by using:
        (1) a sheet-supporting surface, flexible in the directions of test loading on one side of said sheet, comprising:
            (a) a plurality of lateral support leaves capable of being easily flexed in one test direction;
            (b) spacing means at the base of said leaves whereby said leaves are clamped together and supported;
            (c) enclosure means substantially surrounding said leaves such that a specimen in a position to be tested on said leaves comprises a boundary beween said enclosure means at a lower air pressure and the ambient at a higher air pressure, and to which enclosure means said spacing means are attached; and
            (d) aligning means for providing a fixed spacing between said leaves, comprising:
                (1) an alignment frame located inside said enclosure means and surrounding said leaves;
                (2) a plurality of wires stretched across said alignment frame substantially, each wire having one end attached to one side of said alignment frame and the other end attached to the opposite end of said alignment frame, with each wire located between two of said leaves; and (3) means for raising and lowering said alignment frame;

(2) air pressure on the unsupported side of said sheet exceeding that on the supported side of said sheet;

(b) holding said sheet adjacent to said restraining means during testing; and (c) placing a load on said sheet in a desired direction.

4. A method for edgewise compression testing of a flat sheet, comprising:

(a) restraining said sheet from buckling in the lateral direction by using:

(1) a sheet-supporting surface, flexible in the directions of test loading, on one side of said sheet, comprising:

(a) a plurality of semi-rigid columns, free at one end, capable of being easily flexed at their bases in all directions and with the free end of each column having a greater diameter than the other end of each column;

(b) attaching means for fixing the non-free end of said rigid columns;

(c) enclosure means substantially surrounding said columns, such that a specimen in a position to be tested on said columns, comprises a boundary between said enclosure means at a lower air pressure and the ambient at a higher air pressure; and (d) spacing means for ensuring that said columns be spaced evenly across the field of columns, comprising:

(1) an alignment plate located inside said enclosure means, said alignment plate having a plurality of apertures spaced equidistantly thereon, each aperture being of a diameter such that the free end of one of said columns can fit snugly therein; and (2) means for raising and lowering said alignment plate;

(2) air pressure on the unsupported side of said sheet exceeding that on the supported side of said sheet;

(b) holding said sheet adjacent to said restraining means during testing; and (c) placing a load on said sheet in a desired direction.

* * * * *